United States Patent [19]

Viscardi et al.

[11] Patent Number: 5,447,635
[45] Date of Patent: Sep. 5, 1995

[54] PROCESS OF CONCENTRATION AND PURIFICATION OF ORGANIC COMPOUNDS

[75] Inventors: Carlo Viscardi; Rodolfo Piva, both of Milan, Italy

[73] Assignees: Bracco International B.V., Amsterdam, Netherlands; Tecnofarmaci S.p.A., Pomezia, Italy

[21] Appl. No.: 107,799
[22] PCT Filed: Feb. 19, 1992
[86] PCT No.: PCT/EP92/00341
    § 371 Date: Aug. 20, 1993
    § 102(e) Date: Aug. 20, 1993
[87] PCT Pub. No.: WO92/14539
    PCT Pub. Date: Sep. 3, 1992

[30] Foreign Application Priority Data
Feb. 26, 1991 [IT] Italy .................. MI91A0493

[51] Int. Cl.⁶ .................................. B01D 61/14
[52] U.S. Cl. .................. 210/636; 210/641; 210/651; 210/259
[58] Field of Search ........... 210/650, 651, 652, 653, 210/654, 259, 195.2, 636, 641

[56] References Cited

U.S. PATENT DOCUMENTS 5,114,703 5/1992 Wolf et al. .................. 424/5
5,312,615 5/1994 Schneider et al. .......... 424/5

Primary Examiner—Frank Spear
Attorney, Agent, or Firm—Bucknam and Archer

[57] ABSTRACT

A process for the concentration and purification of raw aqueous solutions of water-soluble non-ionic organic compounds, preferably those which are useful as contrast enhancing agents in diagnostic procedures, such as for example X-ray, NMR and ultra-sound diagnosis, through the use of tangential filtration on membranes is described. The process also allows the recovery of valuable reactants in excess and of reaction solvents, if any, and it is particularly useful for purifying expensive non-ionic iodinated compounds, which now have been widely used in X-ray imaging. The filtration plant is described.

17 Claims, 1 Drawing Sheet

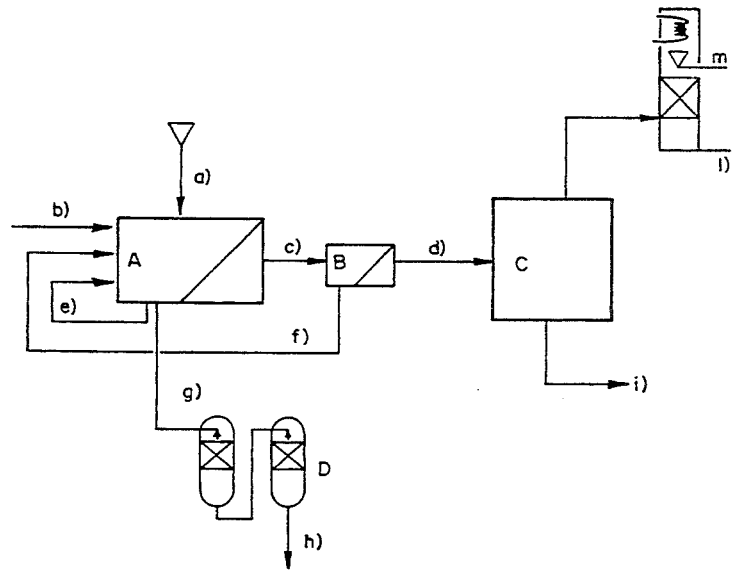

A = Filtrating unit: 1st stage
B = Filtrating unit: 2nd stage
C = Evaporating unit
D = Cationic and anionic resin column
a) = Raw solution of iodinated contrast medium
b) = Make-up water
c) = First permeate (to the second stage)
d) = Final permeate (to the evaporator)
e) = First stage/unit retentate
f) = Second stage/unit retentate
g) = Final retentate (containing the purified contrast medium)
h) = Eluate (to the recovery of the contrast medium)
i) = Residue (to the recovery of valuable compounds)
l) = Reaction solvent (to the recovery)
m) = Water

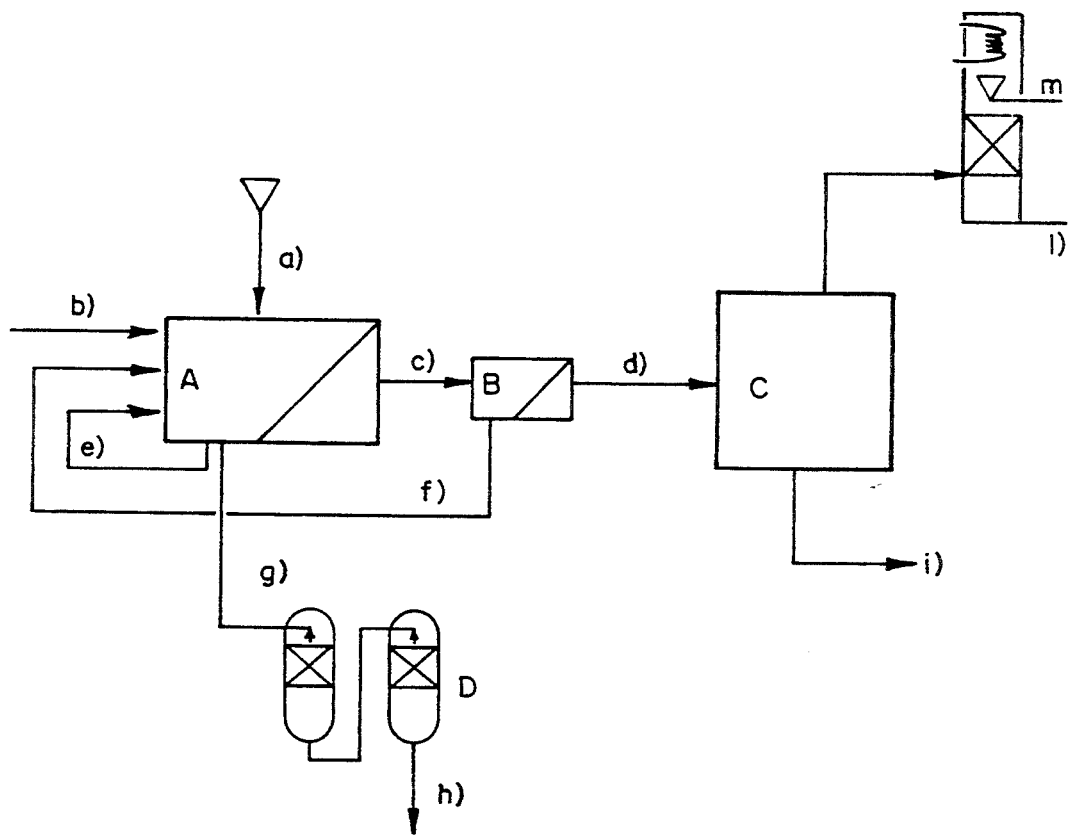

| A | = | Filtrating unit: 1st stage |
|---|---|---|
| B | = | Filtrating unit: 2nd stage |
| C | = | Evaporating unit |
| D | = | Cationic and anionic resin column |
| a) | = | Raw solution of iodinated contrast medium |
| b) | = | Make-up water |
| c) | = | First permeate (to the second stage) |
| d) | = | Final permeate (to the evaporator) |
| e) | = | First stage/unit retentate |
| f) | = | Second stage/unit retentate |
| g) | = | Final retentate (containing the purified contrast medium) |
| h) | = | Eluate (to the recovery of the contrast medium) |
| i) | = | Residue (to the recovery of valuable compounds) |
| l) | = | Reaction solvent (to the recovery) |
| m) | = | Water |

FIG. 1

PROCESS OF CONCENTRATION AND PURIFICATION OF ORGANIC COMPOUNDS

This invention relates to a process aimed at concentrating and purifying raw aqueous solutions of water-soluble non-ionic organic compounds, preferably those which are useful as contrast enhancing agents in diagnostic procedures, such as for example X-ray, NMR and ultrasound diagnosis, through the use of techniques of tangential filtration on membranes. This process also allows the recovery of valuable reactants in excess and of reaction solvents, if any. It is particularly useful for purifying expensive non-ionic iodinated compounds, which now have been widely used in X-ray imaging.

The introduction in X-ray diagnosis of contrast media containing non-ionic iodinated compounds as opacifying agents represented a remarkable progress in the state of this field, so these media will eventually substitute the traditional iodinated ionic products (see: Grainger and Dawson, Clinical Radiology, 1990, 42, 1-5).

However the synthetic processes and, particularly, the final purification of these products are more complex and expensive than those previously used to obtain the ionic contrast media. In fact, neutral iodinated opacifying agents differ from the ionic ones because they cannot be isolated and purified by precipitation from water due to their high solubility in this solvent. Hence, the following problems must still be conveniently solved: the removal of ionic species, usually inorganic salts, present in the final reaction mixture, the recovery of valuable reagents in excess and of the water-soluble reaction media. A preferred technique to be performed (see patents: DE 1909439, GB 1472050, EP 26281) is the one based on the submission of the raw solutions of the contrast media to a complex series of operations such as:

preliminary removal of the solvent, usually dimethylacetamide (DMAC) or dimethylformamide (DMF), by evaporation, dilution by water of the residue, extraction of the residual reaction medium, preferably with a chlorinated solvent, elution of the aqueous phase on a system of columns of cationic and anionic ion-exchange resins, concentration of the eluate by evaporation, crystallization of the crude residue from hydroalcoholic mixtures in order to remove the last neutral impurities.

The drawbacks connected with this type of process are clear. For instance, large purification plants for ion-exchange resins are needed and their running is extremely complex and expensive. In addition, a large quantity of thermal energy is required for the concentration of the considerable volumes of water to be used. It is also necessary to use, to recover and to remove polluting and toxic organic solvents such as the chlorinated ones. Last but not least, the concentration of extremely dilute solutions causes the corresponding concentration of impurity traces and the submission of the final product to a long-lasting thermal treatment.

Another process which can be carried out (see patents: EP 83964, WO 8908101) implies the purification of raw solutions of non-ionic contrast media through preparative liquid chromatography. This technique is extremely complex and expensive too, and in addition it is not suitable for industrial application.

EP 0391621 generically mentions the possibility to use ultrafiltration or column chromatography as an optional further purification step in the preparation of iodized hydroxyethyl starch.

A general treatise of ultrafiltration and reverse osmosis techniques is found in Handbook of Separation Process Technology, R. W. Rousseau ed., John Wiley and Sons, 1987.

The diafiltration process is described for example in Separation Techniques for Chemical Engineers, P. A. Schweitzer ed., McGraw Hill Book Company, 1988.

The process of this invention involves this method on highly concentrated solutions of water-soluble neutral iodinated contrast agents, by obtaining extremely favourable and absolutely unexpected results if compared to the state of the art.

It is known that organic impurities with low relative mass and/or inorganic salts can be removed from aqueous dilute solutions through tangential filtration processes by using ultrafiltration (U.F.) or nanofiltration (N.F.) membranes (Bungay P. M., Lansdale H. K., De Pinho M. N., "Synthetic Membranes: Science, Engineering and Applications", D. Reidel, C 181, 1986 and Applegate L. E., "Membrane Separation Process", Chem. Eng., pages 63-89, 11.06.1984). As these membranes are partially permeable to substances which have relative masses below a given value, part of impurities with lower relative mass permeates together with water, allowing, beyond the concentration of the desired product, a partial purification too. Higher levels of purification can be achieved by performing, subsequently to the concentration state, a dilution stage with water of the non-permeated solution (retentate). This stage, named diafiltration, involves the make-up/dilution of the retentate with de-ionized water. The diluted retentate is filtered again through the filtering membrane in order to allow the permeation of residual impurities.

The main drawback of this method is that, in order to obtain a high level of purity, large amounts of make-up water have to be added to the retentate, i.e. high dilutions are required. That involves considerable equipment size, as a large membrane surface is needed. In addition, if the recovery of some permeated species is needed, and this is the case, the permeate has to be thermally concentrated with heavy energy consumption and thermal stress.

The use of large solvent volumes brings about also a consequent loss of valuable product. The rejections of the membranes, available on the market, to products with relative mass lower than 2000 (such as non-ionic iodinated contrast media) are not sufficiently high, so that the final yield of the purification process is lower than the one obtained through known methods. This flaw is particularly serious because the cost of the product to be purified is very high and yield reductions cannot be accepted.

Another limiting factor of the process is given by the non-feasibility of the separation, if DP, which is the osmotic pressure difference across the membrane (DP corresponds to the difference of osmotic pressure between the retentate and the permeate) exceeds the maximum working pressure of the membrane module, which usually ranges between 2.5 and 4 MPa. On the other hand, it is known (from Bungay P. M., "Synthetic Membranes", cited ref., pages 110-112) that useful permeate flow rates can be obtained only when the working pressure overcomes DP by 1 or 2 MPa. For this reason, solutions recording a DP transmembrane pressure higher than 2.5 MPa are not conveniently purified by nano- or ultrafiltration. In this respect, Table 1 shows the foreseeable situation, considering the cited literature, for a raw solution containing for example, the (L)-5-(2-hydroxy-propionyl)amino-2,4,6-triiodo-bis-(1,3-dihydroxy-isopropyl)isophtalamide
[IOPAMIDOL, Bracco's Patent GB 1472050, Example 1, compound A].

TABLE 1

Foreseeable osmotic and transmembrane pressures for aqueous solutions containing IOPAMIDOL, sodium chloride (NaCl), 2-amino-1,3-propandiol (APD), dimethylacetamide (DMAC), operating at 20° C.

| Components | Foreseen rejections a) | Solution A concentrations (Mol/l) | Solution B concentrations (Mol/l) |
| --- | --- | --- | --- |
| Iopamidol | 0.99 | 0.70 | 0.20 |
| NaCl | 0.20 | 2.10 | 0.60 |
| APD | 0.40 | 1.68 | 0.48 |
| DMAC | 0.30 | 4.58 | 1.31 |
| Total osmotic pressure (MPa) b) | | 26.8 | 7.6 |
| $\Delta$ transmembrane pressure (MPa) c) | | 8.6 | 2.4 | a) rejection values for each component have been derived from the data supplied by the manufacturer of the membrane type which was used (NANOFILM TM NF40, FilmTec Corporation/Dow Chemical), or experimentally from aqueous solutions of the pure components.
b) the osmotic pressure of the solution to be purified has been calculated according to Van't Hoff's equation (Bungay P. M., "Synthetic Membranes", cited ref., pages 109–153).
c) the foreseeable transmembrane pressure has been calculated by the difference between the osmotic pressure the retentate and of the permeate.

When using a solution of Iopamidol 0.7M (Solution A), a very high osmotic pressure and a definitely unfavourable DP transmembrane pressure are foreseen, while the maximum concentration of the same compound, useful in principle for an acceptable purification, is foreseen at 0.2 Mol/l (Solution B). This concentration limit is too low and will eventually have a negative impact on volumes of liquid to be used and consequently on the equipment sizes and the economic running of the same.

One would have expected that ultrafiltration or nanofiltration applied to non-ionic iodinated contrast media solutions would be either impossible due to extremely high pressure, or not competitive in comparison with the known methods when applied to dilute solutions.

SUMMARY OF THE INVENTION

On the contrary, the process of this invention has provided excellent and fully unexpected degrees of purification and recovery of the desired products, thanks to the realization of an innovative filtrating unit which can be run in a non-traditional way, that is, by using highly concentrated solutions of the contrast agent and limited water volumes for the makeup of the retentate while keeping the system working pressure within the usual values for the operation.

BRIEF DESCRIPTION OF THE DRAWING

FIG. 1 illustrates the filtration apparatus according to the present invention.

The filtration apparatus has been built by connecting two filtering groups in series, as shown in the enclosed FIG. 1. The second group is analogous to the first one, but has a smaller size and has been designed to recover the small amounts of the iodinated compound which remain in the permeate from the first stage, without losses of final product. The ratio between the membrane surfaces of the two filtering units (unit one/unit two) can range from 1.5 to 6, preferably from 2.5 to 4. Suitable membranes can be sorted out among the commercial ones featuring a rejection to sodium chloride (measured at concentrations of 2000 ppm, pressure of 1.6 MPa, temperature of 25° C.) not higher than 85%, preferably lower than 70%, and rejection to raffinose higher than 85%, preferably higher than 95%. By way of example, thin-layer membranes can be cited and particularly: TFM TM G-5 (Desal), NANOFILM TM NF40 (FilmTec/Dow Chemical), ROMEMBRA TM SU-200S, SU-220S, SU-600 (Toray), NTR 7410, NTR 4550 (Nitto), MOLSEP TM DRA-4020 (Daicel), OSMOTICS OSMO 411TM012, 411TMX02, 411TBQ01, or asymmetrical polysulphone membranes i.e., PSRO (Millipore). Of course, if the skilled technician uses other types of membranes with similar features, the results are immediate, so, the above mentioned list is absolutely non-limiting for this invention. Tangential filtrating units can be tubular or preferably equipped with flat or spiral wound membranes.

Working temperatures range from 10° C. to 90° C. according to the membrane used, preferably from 25° C. to 45° C.

Working pressures range from 1.5 to 5.5 MPa, preferably from 2 to 3.5 MPa.

The filtering unit is connected to an evaporation-condenser group to recover the solvents, if any, and to concentrate, before their recovery, salts, valuable reactants in excess and reaction by-products, which are in the permeate. In addition, it can be integrated in the latter phase, with a guard of small-volume ion-exchange resins, providing the full elimination of last traces of ionic species, if still present. The running of these columns does not involve substantial energy consumption or considerable extra-costs, due to their limited size.

This filtering unit can be surprisingly run under conditions of extremely high concentrations of the contrast agent. In fact, aqueous solutions to be treated usually contain: non-ionic water-soluble iodinated compounds at concentrations ranging between 15 and 60% in weight (w/w), preferably between 20 and 50%, inorganic salts, such as chlorides, bromides, iodides, sulphites of alkaline or alkaline-earth metals or of ammonium or alkylammonium with a relative mass lower than about 150, organic compounds, generally aminoalcohols with a relative mass lower than about 200, water-soluble solvents, such as for instance dimethylacetamide, dimethylformamide, ethanol, dimethylaminoethanol in concentrations not higher than 25% (w/w), preferably not higher than 15%.

The raw solution containing contrast agent, inorganic salts, organic compounds at a relative mass lower than about 200 and solvents (DMAC, DMF and so on) is pumped on the membranes of the first filtering group. Water, salts, organic compounds at relative mass lower than 200 and solvents, if any, permeate through the membranes and the retentate, partially concentrated and purified as to the contrast agent, is recycled at the first stage after dilution with a little amount of deionized make-up water. The permeate, which still contains small amounts of the iodinated compound, proceeds towards the second filtering group. From here the new retentate is streamed back to the first filtering group in order to fully purify the recovered contrast medium, while the permeate of the second filtering group consists of an aqueous solution of salts, organic compounds to be recovered, solvents, if any, and is contrast-agent free.

This solution is concentrated by evaporation and submitted to the recovery of valuable species in it.

The make-up water, used during the diafiltration stage, does not usually exceed 12 kg per mole of the iodinated compound, preferably is less or equal to 8 kg/mol.

The degree of purification obtained by this process is such that the total amount of residual impurities in the final recycled retentate does not exceed 10% of the initial one, preferably 5%. The filtration parameters, in particular the solution and dilution water feed rates, as well as the retentates flow rates and, of course, the operative pressures, are to be experimentally chosen in correlation with the filtration membranes size and porosity in order to obtain the above mentioned purity degrees.

The final recycled retentate can be percolated, if necessary, on the small guard of columns of ion-exchange resins to remove any traces of inorganic salts before being submitted to crystallization of the final product.

According to the process of this invention the purification levels obtained as a function of the amount of make-up water fed during the diafiltration step, are surprisingly better than the foreseeable ones, as reported in Table 2.

TABLE 2

Percentage residue levels of impurities in an aqueous solution containing Iopamidol, NaCl, APD, DMAC, referred to the amount of the make-up water added per mole of Iopamidol

| Make-up water (I) per mole of Iopamidol | Percentage residue impurities 2) | | | | | |
|---|---|---|---|---|---|---|
| | NaCl b) (rejection 0.2) | | ADP b) (rejection 0.4) | | DMAC b) (rejection 0.3) | |
| | c) | d) | c) | d) | c) | d) |
| 0 | 100 | 100 | 100 | 100 | 100 | 100 |
| 6 | 38.3 | 2.1 | 48.7 | 9.0 | 43.2 | 3.5 |
| 12 | 14.7 | 0.1 | 23.7 | 0.6 | 18.6 | 0.3 | a) calculated by considering equal to 100 the amounts of initial impurity.
b) rejection values for each component have been derived from the data supplied by the membrane manufacturer of NANOFILM ™ NF40, or experimentally by aqueous solutions of the pure component.
c) foreseeable values according to the equation (Aptel P., Clifton M., "Synthetic Membranes", cited ref., pages 249–305):
$C_A = C^°_A \cdot \exp[-V_w/V^° (1-R_A)]$
where:
$V_w$ = make-up water volume
$V^°$ = retentate volume
$C_A$ = concentration of component A
$C^°_A$ = initial concentration of component A
$R_A$ = membrane rejection to component A.
d) experimental values.

The process of this invention allows, for the first time, the concentration and the purification of raw solutions of X-ray water-soluble non-ionic opacifying agents in a simple, economical and environmentally acceptable way.

In particular, it allows higher recovery yields of the contrast compound and the other valuable components, the elimination of large amounts of basic and acid reactants needed for regenerating the ion-exchange resins, beyond their total removal, and a remarkable reduction of the steam necessary for the concentration of the eluates. Finally, it avoids extracting the reaction medium with organic toxic solvents such as chlorinated solvents. All this implies considerable operating advantages from the economical and environmental point of view.

Table 3 shows the advantages that the process of this invention brings to the state of the art for the purification of 1000 kg of Iopamidol.

TABLE 3

Total consumption of the process of desalination of 1000 kg of Iopamidol through tangential filtration and recovery of valuable by-products. Comparison with the state of the art.

| | Process according to the invention kg | Process according to the state of the art kg |
|---|---|---|
| Steam | 9,500 | 16,500 |
| De-ionized water | 10,000 | 83,000 |
| HCl 32% | 720 | 4,000 |
| NaOH 30% | 664 | 4,400 |
| Water cooling | 220,000 | 360,000 |

The process of this invention can be also applied to solutions of any non-ionic water-soluble contrast agents, either for use in X-ray or for use in NMR diagnosis.

In particular it can be preferably applied to the solutions of any non-ionic water-soluble iodinated compounds, even if they are monomers, dimers o trimers.

The following experimental examples describe the advantages of this invention without limiting it. The further possible changes of the indicated parameters are absolutely clear to the skilled technician.

EXAMPLE 1

Purification of (L)-5-(2-hydroxy-propionyl)amino-2,4,6-triiodo-bis-(1,3-dihydroxy-isopropyl)-isophtalamide (Iopamidol: patent GB 1472050, Example 1). 70 kg of an aqueous solution containing 15.5 kg of Iopamidol (22%, w/w), 2.3 kg of sodium chloride, 1.6 kg of sodium acetate, 4.4 kg of 2-amino-1,3-propandiol and 12 kg of dimethylacetamide are fed to the tank of the two-stage filtering plant, which is equipped with a total of 4 m² of a TFM ™ DESAL-G-5 membrane (one 2.5"×40" spiral module for the first stage, and one 2.5"×21" spiral module for the 2nd stage). In a first step (1.5 h), the solution is concentrated up to about 37 kg, by operating at 30° C. at a working pressure of 3 MPa and at a recirculation rate of 750 l/h for both stages. Then, the diafiltration stage begins by continually reintegrating the water through a dosing pump. The process is stopped after 6.5 h when the conductivity falls under 1000 mS/cm and the final retentate, containing 99.6% of the initial Iopamidol (HPLC determination), is percolated on a couple of columns of ion-exchange resins and subsequently crystallized. The pure product 14.6 kg, complying with the requested analytical features (purification yield: 94.2%), are obtained.

The permeate, weighting approximately 120 kg, contains less than 0.4% of the initial Iopamidol and more than 96% of the other initial species in the mixture. The permeate gets through the recovery stage of valuable components. The recovery is quite simple and cheap thanks to the relatively small amount of diluting water.

EXAMPLE 2

Purification of 5-(N-methyl-hydroxyacetyl)amino-2,4,6-triiodo-bis-(2,3-dihydroxy-propyl)-isophtalamide (Iomeprol: EP 26281, Example 11).

50 kg of an aqueous solution containing 14.2 kg of Iomeprol (28%, w/w), 1.9 kg of sodium chloride, 1.5 kg of sodium acetate, 0.9 kg of 1-amino-2,3-propandiol and 15 kg of dimethylaminoethanol are fed to the tank of the filtering unit equipped with 4 m² of NANOFILM TM NF40 membrane in spiral wound modules, as described in Example 1. The purification is carried out in the same way as in Example 1. 13.2 kg of pure product are obtained (overall purification yield: 93%).

EXAMPLE 3

Purification of 1,3-bis-[3-(L-2-hydroxy-propionyl-)amino-5-(1,3-dihydroxy-isopropyl)aminocarbonyl-2,4,6-triiodo-benzoyl-amino]-2hydroxypropane (Italian Patent Application No. 22088 A/90, Example 1).

40 kg of an aqueous solution containing 14.8 kg of the above mentioned product (37% w/w), 1.1. kg of sodium chloride, 2.4 kg of sodium acetate and 0.5 kg of 1,3-diamino-2-hydroxypropane are purified by the procedure described in Example 1. 14.4 kg of pure product are obtained (purification yield: 97.3%).

TABLE 4

Average percentage composition of fluids described in FIG. 1.

| Components | Fluids (% composition in weight) | | | | | | |
|---|---|---|---|---|---|---|---|
| | a) | d) | g) | h) | i) | l) | m) |
| Contrast agent | 25 | traces | 50 | 50 | traces | — | — |
| Inorganic salts | 5 | 4 | traces | — | 25 | — | — |
| Exceeding reactives | 7 | 4 | 1 | traces | 50 | — | — |
| Organic solvent | 13 | 7 | — | — | — | 50 | 1 |
| $H_2O$ | 50 | 85 | 49 | 50 | 25 | 50 | 99 |

We claim:

1. A process for the concentration and purification of a non-ionic water-soluble, iodinated contrast enhancing organic compound from the aqueous solution thereof, said solution having a concentration from 15 to 60% by weight, said solution containing initial impurities, said initial impurities comprising at least one of a) inorganic salts; b) water-soluble residual unconsumed organic reactants at a relative mass lower than about 200; and c) water-soluble organic solvents, the process comprising the following steps:

1) feeding said aqueous solution into a first filtration stage of a two-stage, cascade connected, tangential filtration apparatus, said apparatus comprising two cascade connected filtration stages, said stages having filtration membranes, each of said membranes having a surface, said membranes having a rejection to sodium chloride not higher than 85% and rejection to raffinose higher than 85, whereby a first retentate and a first filtrate/permeate is obtained;

2) passing said first filtrate/permeate from said first stage to said second filtration stage, the ratio of the surface of said filtration membranes between the first and said second stage ranging from 1.5 to 6, whereby a second retentate and a second filtrate/permeate is obtained;

3) continuously recycling said second retentate from said second filtration stage to said first retentate from said first filtration stage into said first filtration stage diluting the resulting retentate with water, the amount of said water not exceeding 12 kg per mole of said organic compound being subject to the purification whereby a third retentate is obtained; and 4) repeating steps 2) and 3) on said third retentate to obtain a degree of purification of said organic compound in the final retentate from said first stage such that the total amount of residual impurities does not exceed 10% of said initial impurities.

2. The process according to claim 1, wherein said step 4) is repeated to reach the total amount of residual impurities not exceeding 5% of said initial impurities.

3. The process according to claim 1, wherein the ratio of said surfaces of said filtration membranes between said first and said second stage ranges from 2.5 to 4.

4. The process according to claim 1, wherein said membranes have a rejection to sodium chloride not higher than 70% and rejection to raffinose higher than 95%.

5. The process according to claim 1, wherein the temperature of said first and second stage ranges from 10° to 90° C.

6. The process according to claim 5, wherein the temperature of said first and second stage ranges from 25° to 45° C.

7. The process according to claim 1, wherein the pressure applied to said first and second stage ranges from 1.5 to 5.5 MPa 8. The process according to claim 7, wherein the pressure applied to said first and said second stage ranges from 2 to 3.5 MPa.

9. The apparatus according to claim 1, wherein said filtration apparatus is connected to an evaporation-condenser group to recover volatile components from said permeates from said second stage.

10. The process according to claim 1, wherein said final retentate is passed through a guard of anionic and cationic ion-exchange resins.

11. The process according to claim 1, wherein in step 3) said amount of water does not exceed 8 kg per mole of said organic compound.

12. The process according to claim 1, wherein the nonionic water-soluble, iodinated contrast enhancing organic compund is the X-ray opacifying agent (1)-5-(2-hydroxy-propionyl)amino-2,4,6-triiodo-bis-(1,3-dihydroxy-isopropyl) isophtalamide.

13. The process according to claim 1, wherein the non-ionic water-soluble, iodinated contrast enhancing organic compound is the X-ray opacifying agent 5-(N-methyl-hydroxyacetyl)amino-2,4,6-triiodo-bis-(2,3-dihydroxypropyl)isophtalamide.

14. The process according to claim 1 wherein the non-ionic water-soluble, iodinated contrast enhancing organic compound is the X-ray opacifying agent 1,3-bis-[3-(L-2-hydroxy-propionyl)amino-5-(1,3-dihydroxy-isopropyl)amino-carbonyl-2,4,6-triiodo-benzoyl-amino]-2-hydroxypropane.

15. A two-stage tangential filtration plant for the concentration and purification of the solution of a non-ionic, water-soluble iodinated contrast enhancing organic compound, said plant comprising two filtrating stages (A) and (B) connected in series, each of said stages having a filtration membrane, each filtration membrane having a surface, the ratio of the filtrating membrane surfaces between said first stage (A) and said second stage (B) ranging from 1.5 to 6, an inlet for feeding said first stage (A) with said solution of said iodinated organic compound, an inlet for the second stage, an outlet from the first stage for each of the first retentate and the first permeate, an outlet from the second stage for each of the second retentate and the second permeate;

the retentate outlet of said first stage (A) is connected by means of a first recycling circuit e) to said first stage (A);

the permeate outlet of said first stage (A) is connected to said feed inlet of said second stage (B) by means of a second circuit c);

the second retentate outlet of said second stage (B) is connected by means of a third recycling circuit (f) to said first stage (A);

said first stage (A) is provided with a connection for the make-up water line (b);

the permeate outlet of said second stage (B) goes to waste or to a secondary recovery system through a fourth circuit (d);

the final retentate outlet of said first stage (A) is transmitted to the main recovery circuit (g) for the recovery of the purified iodinated compound.

16. The filtration plant according to claim 15 wherein the permeate outlet of said second stage (B) is connected through said circuit (d) to an evaporating unit, (c) said evaporating unit being equipped with a condensing unit.

17. The filtration plant according to claim 15 wherein the third retentate outlet of said first stage (A) is connected through said circuit (d) to a guard of anionic and cationic resins.

* * * * *

UNITED STATES PATENT AND TRADEMARK OFFICE
CERTIFICATE OF CORRECTION

PATENT NO. : 5,447,635
DATED : September 5, 1995
INVENTOR(S) : Carlo Viscardi, et al It is certified that error appears in the above-identified patent and that said Letters Patent is hereby corrected as shown below:

In claim 12:   "(1)-5-(2-hydroxy..."   should read:
(Col. 8, Line 37)
              --(L)-5-(2-hydroxy...--

In Claim 17:   "circuit (d)..."   should read:
(Col. 10, Line 11)
              --circuit (g)...--

Signed and Sealed this

Twenty-third Day of January, 1996

Attest:

BRUCE LEHMAN

*Attesting Officer*     *Commissioner of Patents and Trademarks*